(12) United States Patent
Spangler et al.

(10) Patent No.: US 6,841,149 B1
(45) Date of Patent: Jan. 11, 2005

(54) PROBIOTIC MIXTURE INTENDED FOR MONOGASTRIC ANIMALS TO CONTROL INTESTINAL FLORA POPULATIONS

(75) Inventors: David A. Spangler, Sterling, IL (US); Patrick K. Brown, Camanche, IA (US); Thomas E. Witzig, Rochester, MN (US)

(73) Assignees: Agri-King, Inc., Fulton, IL (US); Mayo Foundation for Medical Education and Research, Rochester, MN (US)

( * ) Notice: Subject to any disclaimer, the term of this patent is extended or adjusted under 35 U.S.C. 154(b) by 68 days.

(21) Appl. No.: 10/202,159

(22) Filed: Jul. 24, 2002

Related U.S. Application Data

(63) Continuation-in-part of application No. 09/087,792, filed on May 29, 1998, now Pat. No. 6,524,574.

(51) Int. Cl.[7] .............................................. A01N 63/00
(52) U.S. Cl. ................ 424/93.3; 424/93.45; 424/93.51; 424/93.48; 435/252.4
(58) Field of Search ............................ 424/93.3, 93.45, 424/93.51, 93.48; 435/252.4

(56) References Cited

U.S. PATENT DOCUMENTS 5,501,857 A * 3/1996 Zimmer ...................... 424/438
6,221,350 B1 4/2001 Brown et al.
6,524,574 B1 * 2/2003 Spangler et al. ........... 424/93.3

OTHER PUBLICATIONS

ATCC Catalogue. ATCC Bacteria and Bacteriophages. 19th edition. 1996. American Type Culture Collection. pp. 136, 137 and 346.*
"Strategic Options to manipulate the intestinal microbial activity in weanling pigs", by Dr. Pat Brown, Nov. 1997, vol. 22. "Viewpoint". Ed.: P. Bogis. pp. 1 and 6.
Sales of probiotic product (MGP) in Jun., 1997: Computer run showing First Invoicing of Dominate Products VS MGP of Jun. 2, 1997.
Copy of Swine–MGP flyer which includes a copy of the product label dated Dec. 29, 1997.

* cited by examiner

Primary Examiner—Vera Afremova
(74) Attorney, Agent, or Firm—Brian J. Laurenzo; Jason M. Hunt; Michael C. Gilchrist

(57) ABSTRACT

A mixture of probiotics effective to reduce the contamination of enteric bacteria in humans and other monogastric animals. The mixture of probiotics includes one or more acid-producing bacteria strains and one or more yeast strains, and may advantageously be supplemented with a source of nutrients, such as prebiotics including fructo-oligosaccharides. In a preferred embodiment, said one or more bacteria strains contain *Enterococcus faecium* strain NCIMB #10415, and said one or more yeast strains contain NCYC #47 and CNCM I-1079.

4 Claims, 8 Drawing Sheets

PROBIOTIC MIXTURE INTENDED FOR MONOGASTRIC ANIMALS TO CONTROL INTESTINAL FLORA POPULATIONS

This application is a continuation-in-part of U.S. application Ser. No. 09/087,792, filed May 29, 1998, now U.S. Pat. No. 6,524,574 entitled PROBIOTIC MIXTURE INTENDED FOR MONOGASTRIC ANIMALS TO CONTROL INTESTINAL FLORA POPULATIONS, which is hereby incorporated by reference.

BACKGROUND OF THE INVENTION

1. Field of the Invention

The invention relates to a mixture of probiotics to be fed to monogastric animals and, more specifically, a mixture of facultative anaerobic probiotic organisms affecting and controlling or inhibiting the colonization of deleterious bacteria in the intestines of monogastric animals and humans.

2. Background of the Invention

Probiotics are defined as microbes that are fed to animals to improve the microbial populations in the intestines of animals or humans. Most prior art probiotics are lactic acid-producing bacteria. The probiotics of the present invention include both bacteria and yeasts.

Probiotics have been fed to animals to reduce or replace the potentially pathogenic intestinal bacteria with nonpathogenic species.

Spring, March 1997; (Animal Talk), opines that the main regulatory mechanisms used by natural gut inhibitants as Lactobacilli and Enterococci is to keep pathogenic bacteria from colonizing the digestive tract. Mechanisms discussed include competition for nutrients, growth factors, intestinal receptor sites, and stimulation of epithelial cell turnover. Creation of a restrictive environment includes lower pH, VFA and lactic acid production or induction of an immunologic process or antimicrobial substances.

Presser, et al, 1997 (Appl & Environ Microbio Vol. 63 No. 6:2355–2360), observed the negative effects on the growth rate of *E. coli* as a function of pH and lactic acid concentration. The findings demonstrated *E. coli* growth rate was linearly related to the hydrogen ion concentration. In the range 0 to 100 mM lactic acid, growth rate was also linearly related to the undissociated lactic acid concentration.

Hudault et al., 1997 (Appl & Environ Microbio Vol. 63 No. 6:513–518) demonstrated an antagonistic activity exerted in vitro and in vivo by *Lactobacillus casei* (strain GG) against *Salmonella typhimurium* C5 infection. The mechanism of this antagonist activity was reported to be dependent upon an acidic environment due to lactic acid itself or alternatively to a substance that is active at low pH.

Kimura, et al., 1997 (Applied and Environmental Microbiology Vol. 63, No. 9:3394–3398) found that human test subjects harbored a unique collection of Bifidobacteria and Lactobacilli species. Their results emphasized the complexity of the relationship between the intestinal microflora and the host where it appears that the host's predominant strains do not illicit as large of a IgG titer response as do nondominant intestinal species.

Perdigon, et al., 1991 (J Dairy Research Vol. 58:485–496) showed an immunoadjuvant activity of oral *Lactobacillus casei* by playing an important role in the prevention of enteric infections by increasing IgA secretion into the intestinal lumen thus providing a defense for the mucosal surface against enteric (i.e., *Salmonella* and *E. coli*) challenges.

Bernet, et al., 1994 (Gut 35:483–489) demonstrated *Lactobacillus acidophilus* LA1 binds to cultured human intestinal cell walls and inhibits cell attachment and cell invasion by enterovirulent bacteria.

Fujiwara, et al., 1997 (Appl & Environ Microbio Vol. 63 No. 6:506–512) showed that the binding inhibitor produced by *B. longum* and other *Bifidobacterium* species was estimated to contribute to their normal anti-infectious activities by preventing the binding of pathogenic strains of *E. coli* to their common bacterium intestinal binding structures.

Firon, et al., 1983 (Carbohydrate Res. 120:235–249) commented on carbohydrate specificity of the surface lectins of *Escherichia, Klebsiella,* and *Salmonella* organisms.

Adlerberth, et al., 1996 (Appl & Environ Microbio Vol. 63 No. 6:2244–2251) found mannose-specific adhesions in a variety of gram-negative bacteria including members of the family Enterobacteriaceae such as *Escherichia, Shigella, Enterobacter, Klebsiella,* and *Salmonella* and in. *Pseudomonas* and *Vibrio*.

Adlerherth, et al., also found that Saccharomyces species of yeast contain mannosE-containing polysaccharides in their cell walls which *E. coli* and other intestinal bacteria adhere to in a mannose-specific manner.

Jonvel, 1993 (Feed Mix Vol. 1, No. 4) citing Gedek, stated there are three possible explanations of *Saccharomyces* yeasts' mode of action: 1) fixation of *E. coli* on the yeast cell wall surface if *E. coli* has fimbria (i.e., the fimbria have an affinity to mannose); 2) fixation of enterotoxin on the yeast cell wall surface and are destroyed; and 3) *E. coli* destruction by lethal yeast toxin.

Abe, et al. (1995. J Dairy Science 78:2838–2846) showed that probiotics fed to newborn calves and piglets decreased frequency of diarrhea, and stimulated body weight gains and feed conversion in those animals over control animals.

Saavedra, et al., 1994 (Lancet 334:1046–1049) showed that feeding of a *Bifidobacteria* and *Enterococci* species to hospitalized human infants for prevention of diarrhea and the shedding of rotavirus.

Ozawa, et al. 1983 (Applied and Environmental Microbiology 45: 151) reported that the administration of an *Enterococcus* species to calves and piglets promoted colonization of beneficial bacteria and decreased the occurrence of detrimental bacteria, such as *Salmonella,* in the intestine.

Surawiciz, et al., 1989 (Gastroenterology Vol. 96, No. 4: 961–968) showed that *Saccharomyces boulardii* significantly reduced the incidence of antibiotic-associated diarrhea in hospitalized patients. *S. boulardii* has antagonistic activity against a variety of bacterial pathogens. In rats and humans it increases the disaccharidase activity in intestinal mucosa which, in turn, may improve carbohydrate absorption within the host.

From the *Bergey's Manual of Systematic Bacteriology* 1984. it is observed that within the genera *Campylobacter, Pseudomonas* and most *Vibrio* and *Clostridia* species do not utilize lactose as a carbon source for growth. Also, Enterobacteriaceae, in general, are poor or nonutilizers of lactose. Whereas, the *Enterococcus* species used in the invention readily utilize lactose.

The importance of mannose-sensitive adhesions of gram-negative intestinal bacteria for intestinal colonization of these bacteria was investigated, as well as the presence of a mannose-specific adhesion in a gram-positive bacterial species, i.e., *Lactobacilli* and *Enterococci*, which belong to the indigenous intestinal microflora. Further, investigation was made into the ability of gram-positive, non-pathogenic *Enterococci* and *Lactobacilli* to associate with animals' intestines and mannose containing polysaccharides (mannans) found as a major cell wall component in species of *Saccharomyces*, and, in particular, its use in conjunction with the lactic acid-producing metabolism of *Enterococci* and/or *Lactobacilli* to rid and/or prophylatically protect the intestines of monogastric animals and humans of potentially pathogenic enteric microorganisms.

SUMMARY OF THE INVENTION

The invention consists of a defined combination of facultative anaerobic probiotic organisms effective in controlling or inhibiting the colonization of certain deleterious bacteria in the intestines of monogastric animals and humans. In a preferred embodiment of the invention, nutrients are added to the mixture of probiotics to enhance efficacy in some situations.

The invention is a unique probiotic mixture that combines viable lactic acid-producing *Enterococcus* strains and viable *Saccharomyces* yeast strains that are preferably added to an active carrier that includes nutrients to assist in the growth and/or activity of the probiotics. The mixture is fed to monogastric animals to control the microflora population of the intestinal tract and to maintain a proper balance of naturally occurring beneficial microflora while competing with and helping to exclude deleterious strains of microflora such as bacterial pathogens, thus aiding the ability of the animal to maintain a normal, healthy intestinal environment and, in turn, utilize feeds better.

Ingesting this probiotic mixture by monogastric animals and humans will help the body protect itself from colonization of pathogenic microflora such as bacteria within the families Enterobacteriacae and Vibrionaceae, and the genera *Campylobacter, Clostridium, Pseudomonas,* or other organisms that can cause intestinal distress.

An object of the present invention is to provide a mixture of probiotics, which is orally administered to monogastric animals to assist the animal in protecting itself from the colonization and reproduction of pathogenic microorganisms.

Another object of the invention is to provide a mixture of probiotics for the oral administration to humans, which will treat and provide a prophylactic effect on microorganisms which cause diarrhea and other intestinal distresses.

These and other objects of the invention will be made apparent to one of skill in the art upon a review and understanding of the specification, the associated drawings, and appended claims.

DETAILED DESCRIPTION OF PREFERRED EMBODIMENTS

Figure 1:
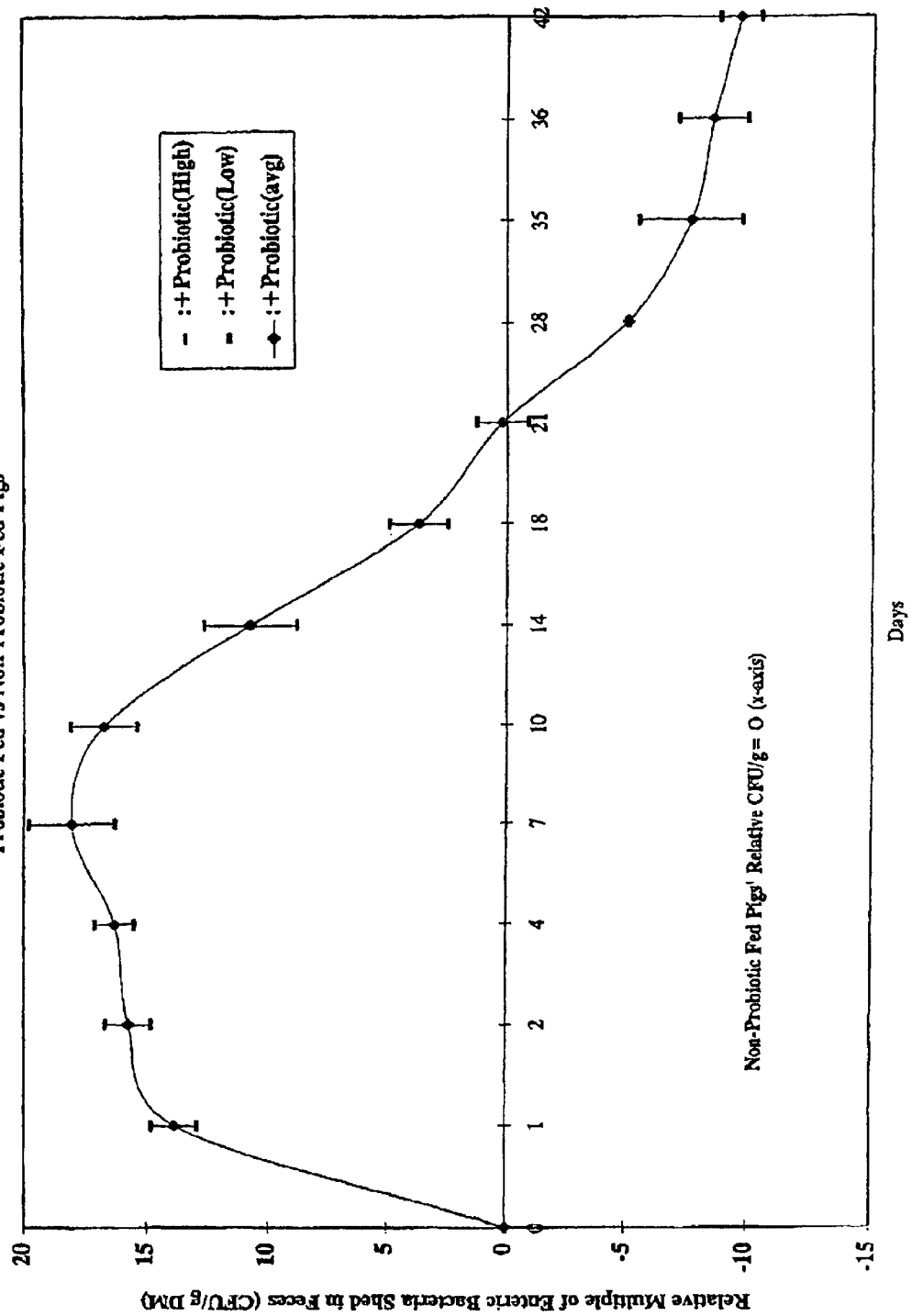
FIG. 1 is a graphical representation of the relative shed of enteric bacteria over time by swine following administration of a probiotic mixture of the present invention.

The present invention provides a method of delivering a mixture of probiotics to the intestines of monogastric animals in order to establish a population of microflora that will out-compete deleterious microbes for intestinal nutrients and impede the adherence of deleterious bacteria to the intestinal wall. It also provides viable yeast microbes that will attract and attach these deleterious microbes to the yeast's cell surface and carry them out of the body as excrement. A food source that enhances the growth of the invention's microbes but is not an effective nutrient for the pathogenic microflora may be included to assure growth and metabolism of the probiotic organisms.

Microflora such as the *Enterococci* of our invention effectively colonize the animal's intestines. Pathogenic microflora such as *Escherichia, Shigella, Enterobacter, Klebsiella, Pseudomonas, Salmonella* and *Vibrio,* attach to mannose receptor compounds in the cell walls of intestinal villi. They use mannose sugars as recognition compounds for attachment onto the mucosal cells. The aforementioned pathogenic microbes prefer a relatively low acid (neutral pH) environment while the microbes of our invention prefer a more acidic environment.

The lactic acid-producing *Enterococci* of our invention readily use lactose as a source of food for growth and reproduction. The aforementioned deleterious microbes do not utilize lactose as well as the microbes in our invention thus resulting in a competitive starvation for this food source. Accordingly, a source of lactose or other carbohydrate or nutrient may be advantageously included in the probiotic mixture.

Once the *Enterococcus* organisms of our invention inhabit the animal's intestine, they begin to metabolize, reproduce and produce lactic acid, which is excreted into the surrounding environment. The lactic acid lowers the pH in the area causing the neighboring harmful enteric organisms to detach from their locations on the intestinal villi due to the acidic environment.

Subsequent to the detachment from the villi attachment sites, the enteric microbes encounter the yeast strains, which, like the intestinal villi, contain mannose receptor compounds in their cell walls. The aforementioned deleterious microbes use these mannose sugars as recognition compounds for attachment onto the intestinal villi. Even if the pathogenic bacteria prefer the receptor sites on the intestine over those of the yeast, the production of a poor environment for these microflora by the *Enterococci* via acid produced leads to the detachment of the pathogenic bacteria and their subsequent adherence to the yeast strains is observed.

The invention's yeasts do not adhere to intestinal walls and therefore, maintain themselves in the intestinal lumen where they pass through and are excreted in the manure. This passage carries any attached enteric microflora from the body.

The probiotic contains a combination of viable lactic acid-producing bacteria (including the genera *Enterococcus* and *Lactobacillus*) and a viable yeast (of the *Saccharomyces* genera, which have mannose-containing polysaccharides and glucans associated with their cell walls). A carbohydrate source (including whey, milk products, and lactose) which is poorly utilized by many pathogenically significant species of the families Enterobacteriaceae and Vibronaceae, and the genera *Pseudomonas, Campylobacter* and *Clostridium,* may be advantageously included with the bacteria and yeast. The lactic acid-producing bacteria and yeast strains of the probiotic mixture grow best under mesophilic temperatures (25° C. to 40° C.) and slightly acidic conditions (pH 6.8 to 5.0), even though growth can be observed within the range of pH=4.0 to 8.0 with the lactic acid-producing bacteria and within the range of pH=3.5 to 8.0 with the yeasts.

In the present invention, the combination of yeast and acid-producing bacteria in a single probiotic product produces an unexpected, synergistic probiotic effect. In a substantial number of cases, the probiotic effect increases at least 5-fold when both yeast and acid-producing bacteria are used in the probiotic composition. In certain cases, the probiotic effect increases at least 10-fold. This synergistic effect does not depend on the use of specific strains or species of yeast and acid-producing bacteria. Various strains and species of yeast and acid-producing bacteria can be used to produce the synergistic effect.

In one embodiment, no less than 3% of the total viable CFUs in the probiotic composition are yeast CFUs, and no greater than 97% of the total viable CFUs in the probiotic composition are acid-producing bacteria CFUs. Preferably, between 5% and 70% of the total viable CFUs are yeast CFUs, and between 30% and 95% of the total viable CFUs are acid-producing bacteria CFUs. For instance, the yeast CFUs can constitute between 5% and 50% of the total viable CFUs, and the acid-producing bacteria CFUs constitute between 50 and 95% of the total viable CFUs. For another instance, the yeast CFUs constitute between 5% and 40%, between 5% and 30%, or between 10% and 20% of the total viable CFUs, and the acid-producing bacteria CFUs constitute between 60% and 95%, between 70% and 95%, or between 80% and 90%, respectively, of the total viable CFUs.

Preferably, the total viable yeast and acid-producing bacteria CFUs in the probiotic composition are at least $1 \times 10^5$ CFU/g. More preferably, the total viable yeast and acid-producing bacteria CFUs are at least $1 \times 10^6$ CFU/g, such as $1 \times 10^7$ or $1 \times 10^8$ CFU/g. Highly preferably, the total viable yeast and acid-producing bacteria CFUs are at least $1 \times 10^9$ CFU/g. In one embodiment, the total viable yeast and acid-producing bacteria CFUs are at least $1 \times 10^{10}$ CFU/g.

Suitable yeast for this invention include, but are not limited to, various *Saccharomyces* species, such as *Saccharomyces cerevisiae* (e.g. strain ATCC#32167), *Saccharomyces bayanus* (e.g. strain ATCC #36022) and *Saccharomyces boulardii*. Different yeast species or strains can be used alone or in combination with other yeast species or strains. Suitable acid-producing bacteria include, but are not limited to, various *Bifidobacteria, Lactobacilli* and *Enterococcus* species, such as *Bifidobacterium longum* (e.g. strain ATCC # 15707), *Bifidobacterium breve* (e.g. strain ATCC # 15700), *Bifidobacterium infantis* (e.g. strain ATCC # 15697), *Bifidobacterium adolescentis* (e.g. strain ATCC # 15703), *Lactobacillus rhamnosus* (e.g. strain NCIMB # 8103), *Lactobacillus acidophilus* (e.g. strain ATCC # 521), *Lactobacillus casei* (e.g. strain ATCC # 4913), *Lactobacillus bulgaricus* (e.g. strain ATCC # 11842), *Lactobacillus gasseri* (e.g. strain ATCC # 11718), *Enterococcus faecium* (e.g. strain NCIMB #10415, supplied by Cerbios-Pharma, S A, Barbengo, Switzerland; strain WN, commercially available from Loders Croklaan, Inc., 24708 W. Durkee Rd., Channahon, Ill. 60410: and strain NCIMB Accession No. 11181, commercially available from Medipharm, USA, 10215 Dennis Drive, Des Moines, Iowa 50322), *Enterococcus casseiflavus* (e.g. strain ATCC #51328, supplied by the American Type Culture Collection (ATCC), Manassas, Va.), and *Enterococcus avium* (e.g. strain ATCC #14025). Different acid-producing bacteria species or strains can be used alone or in combination with other acid-producing bacteria species or strains.

In one embodiment, the probiotic composition contains at least two different *Saccharomyces* yeast strains, which may belong to the same or different species. In another embodiment, the probiotic composition contains at least two different *Enterococcus* bacteria strains, which may belong to the same or different species. A preferred probiotic composition contains one *Enterococcus faecium* strain (e.g. strain NCIMB #10415) and two different *Saccharomyces* strains (e.g. strains NCYC #47 and CNCM I-1079).

As used herein, "ATCC" refers to American Type Culture Collection (ATCC) at 10801 University Blvd., Manassas, Va. 20110-2209, USA. "NCYC" refers to National Collection of Yeast Cultures (NCYC) at AFRC Institute of Food Research, Norwich Laboratory, Colney Lane, Norwich NR4 7UA, United Kingdom. "CNCM" refers to Collection Nationale De Cultures, De Micro-organismes (CNCM) at Institut Pasteur, 28, rue du Dr Roux, 75724 Paris Cédex 15, France. "NCIMB" refers to National Collections of Industrial, Food and Marine Bacteria (NCMB) at 23 St. Machar Drive, Aberdeen AB2 1RY, Scotland, United Kingdom.

In another embodiment, at least 80% of the total viable CFUs in the probiotic composition are *Saccharomyces* yeast CFUs and *Enterococcus* bacteria CFUs. More preferably, at least 85%, 90%, 95% or 99% of the total viable CFUs in the probiotic composition are *Saccharomyces* yeast CFUs and *Enterococcus* bacteria CFUs. In a preferred embodiment, at least 80%, 85%, 90%, 95% or 99% of the total viable CFUs in the probiotic composition are *Saccharomyces cerevisiae* yeast CFUs and *Enterococcus faecium* bacteria CFUs.

The carbohydrate source in the probiotic composition preferably contains prebiotics. As used herein, prebiotics refers to food ingredients which are ingested by the monogastric animal/human and reach the large intestine undigested and can be used as a nutrient source to promote the growth or metabolic activities, or both, of acid-producing bacteria in the large intestine. The. probiotic product composition may contain one or more prebiotic components. In one embodiment, the prebiotic component(s) constitute at least 5% by weight of the total mass of the probiotic product composition. For instance, the prebiotic component(s) can constitute at least 10, 15, 20, 25, 30, 35, 40, 45, or 50% by weight of the total mass of the probiotic product composition. Preferably, the prebiotic component(s) constitute more than 50% by weight of the total mass of the probiotic product composition, such as more than 60%, 70%, 80%, 90%, 95% or 99%.

Acid-producing bacteria, such as *Bifidobacteria, Lactobacilli* and *Enterococci,* can readily use and/or metabolize these prebiotic components in the large intestine to produce, for example, short chain fatty acids (SCFA). These acid-producing bacteria are aciduric, and therefore, can flourish in the large intestine in the presence of SCFA. In contrast, enteric bacteria, such as those in the family of *Enterobacteriaceae, Vibrio, Campylobacter* and *Clostridia* species, do not grow well under the similar conditions because of their sensitivity to acidic environment.

Suitable prebiotic components for the present invention include, but are not limited to, fructo-oligosaccharides, gluco-oligosaccharides, galacto-oligosaccharides, isomalto-oligosaccharides, xylo-oligosaccharides, or soybean oligosaccharides. As used herein, an "oligosaccharide" is a chain of at least three monosaccharide units. The oligosaccharide chain can be either linear or branched. In a preferred embodiment, the oligosaccharide contains between 3 and 60 monosaccharide units. Oligosaccharides containing more than 60 monosaccharide units may also be used in the present invention.

Fructo-oligosaccharides include linear or branched fructose oligomers, which can be either $\beta$-2,1-linked inulins or $\beta$-2,6-linked levans, or both. The degree of polymerization of the preferred fructo-oligosaccharides ranges between 2 to 60 fructose units with a terminal glucose unit. Examples of gluco-oligosaccharides include $\beta$-glucobiose and $\beta$-glucotriose, in which two or three molecules of glucose are linked by a $\beta$-1,6-linkage. Preferred galacto-oligosaccharides include a chain of one to four galactose units, which is linked to the galactose residue of lactose. At least two types of galacto-oligosaccharides can be used in the present invention, one containing the $\beta$-1,4 galactose linkage and the other containing the $\beta$-1,6-linkage. Examples of isomalto-oligosaccharides include isomaltotri-ose and panose. Examples of xylo-oligosaccharides include xylobiose and xylotriose, such as those produced by enzymatic hydrolysis of hemicellulose. Preferred soybean oligosaccharides are raffinose and stachyose, in which one or two molecules of galactose are linked to the glucose residue of sucrose via a $\alpha$-1,6-linkage. All of the above-described oligosaccharides can be used alone or in combination with other oligosaccharides or other prebiotic components.

Monosaccharides and/or disaccharides can also be used as the carbohydrate source in the probiotic composition of this invention. Suitable monosaccharides and disaccharides include, but are not limited to, arabinose, fructose, galactose, glucose, lactose, maltose, mannose, ribose, lactulose and sucrose. Lactulose is a lactose derivative in which the glucose residue of lactose is replaced by fructose. In addition, sorbitol may be used as the carbohydrate source. Preferably, these carbohydrate sources constitute at least 5% by weight of the total mass of the probiotic composition. For instance, they can constitute at least 10, 15, 20, 25, 30, 35, 40, 45, or 50% by weight of the total mass of the probiotic composition. Preferably, they constitute more than 50% by weight of the total mass of the probiotic composition, such as more than 60%, 70%, 80%, 90%, 95%, or 99%. These carbohydrate sources can be used alone or in combination with other carbohydrate sources including oligosaccharide prebiotics.

In one embodiment, the probiotic mixture contains between about 20% and about 70% of the *Saccharomyces* yeast CFUs and between about 30% and about 80% of the *Enterococci* bacteria CFUs, and preferably between about 30% and about 50% of the *Saccharomyces* yeast CFUs and between about 50% and about 70% of the *Enterococci* bacteria CFUs, with the preferred embodiment comprising 40% *Saccharomyces* and 60% *Enterococci.* In particular, the commercial products of the probiotic mixture according to this embodiment contained equal quantities of the two *Enterococcus* strains, *Enterococcus faecium* NCMIB Accession No. 11181, and *Enterococcus faecium* strain NCIMB #10415, and equal quantities of the two *Saccharomyces* strains, *Saccharomyces* strains identified with the accession numbers NCYC # 47 and CNCM I-1079. The commercial products incorporating the probiotic mixture of the present invention are administered to provide at least $10^9$ CFUs of the *Saccharomyces* yeast and lactic acid-producing *Enterococci* combination is ingested per head per day and no adverse effects have been observed at administration rates up to $100 \times 10^9$ per head per day. Below about $1 \times 10^8$ CFUs per animal per day the results become variable and full efficacy may not be observed. The lactose source used in the commercial products is high-lactose whey that is available from a variety of commercial sources. In the experiments set out in this specification, the specific high-lactose whey was specified to contain between 80.0% and 88.0% lactose, between 3.0% and 5.0% crude protein, a maximum of 8.5% ash and a maximum of 5% moisture. A commercial product is constituted with the strains of *Saccharomyces* and *Enterococci* as set out above added to the high-lactose whey in amounts so that there is a total of $150 \times 10^9$ CFUs of the yeast and bacteria in 1 lb. of the commercial product.

EXPERIMENT 1

The effect of the probiotic mixture on the shedding of enteric bacteria (such as Gram-negative bacilli) by pigs from 50 lbs. market weight was the subject of a trial. Nine hundred, fifty (950) 50 lb. pigs were fed a control ration consisting of a commercially accepted swine ration. Nine hundred, fifty (950) 50 lb. pigs were fed the control ration supplemented with 2 lbs. per ton of the mixture of probiotics identified above. Manure was randomly collected from 5 animals from each group, composited, and analyzed to determine the amount of enteric bacteria shed and the feed utilization of the animals.

TABLE 1

Analyzed values of the manure (dry matter basis) of 50 lb. to 250 lb. pigs comparing control diet and diet including mixture of probiotics

| Analysis | Day 1 50 lb. pig Control Feces | Day 1 50 lb. pig Probiotic Feces | Day 100 "250 lb. pig" Control Feces | Day 100 "250 lb. pig" Control Feces | Day 100 "250 lb. pig Probiotic Feces |
|---|---|---|---|---|---|
| % Starch | | | 62.79 | 5.01 | 3.68 |
| % Calcium | | | 0.54 | 1.95 | 1.10 |
| % Phosphorus | | | 0.37 | 2.64 | 2.25 |
| % Magnesium | | | 0.12 | 1.13 | 1.10 |
| pH | 6.6 | 6.6 | 6.0 | 6.4 | 6.0 |
| Enteric CFU/g | 177,000 | 2,720,000 | 0 | 1,740,000 | 125,000 |

Figure 2:
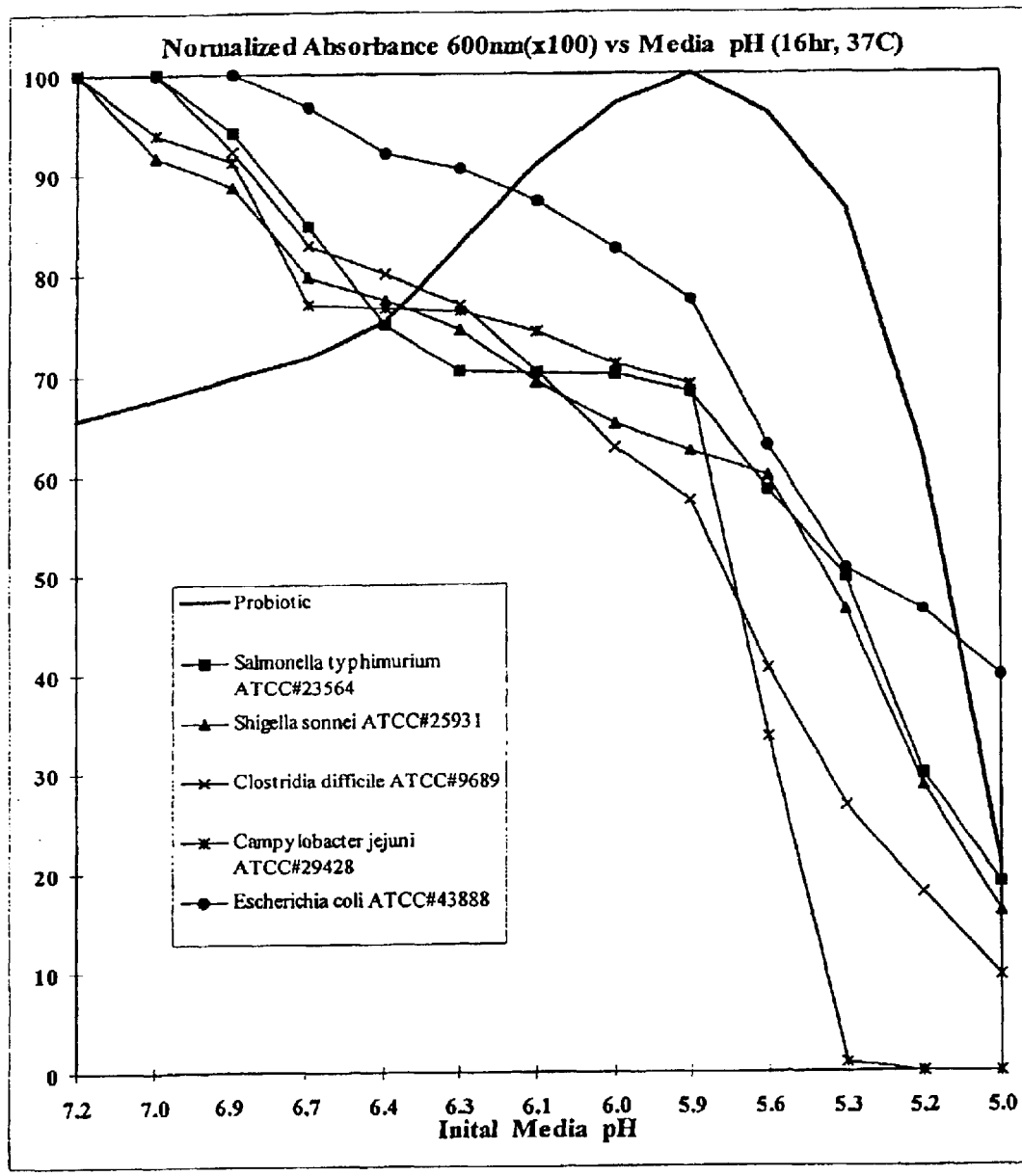
FIG. 2 is a graphical representation of the percent growth of enteric gut pathogens over a pH range and comparing the growth rate of the mixture of probiotics of the present invention.

There is observed in the data of Table 1 a marked increase in the number of enteric bacteria shed in the first day following administration of the probiotic mixture of the present invention into the ration of the test animals. There is also a marked decrease in the number of enteric bacteria shed after 100 days of treatment. Further, enhanced feed utilization is seen in the reduced amount of starch and minerals that remain in the feces of the animals being fed the mixture of probiotics of the present invention. The fecal pH of the test animals is also reduced, resulting in an environment which prefers growth of the probiotics while relatively inhibiting the growth of the enteric bacteria (see FIG. 2). The culture media used in the tests of FIG. 2 is set out in Table 2.

TABLE 2

Culture Media Substrate
(pH adjusted from 7.2 through 5.0 with 12N hydrochloric acid)

| Media (Ingredient) | Per liter (grams) |
|---|---|
| Bacto-Soytone (Difco) | 15.0 |
| Dextrose | 6.0 |
| Maltose | 6.0 |
| Sodium Chloride | 5.0 |
| Dipotassium phosphate | 5.0 |
| Monopotassium phosphate | 1.0 |
| Monosodium phosphate | 3.0 |
| De-ionized water | 1,000.0 |

EXPERIMENT 2

A similar trial was conducted on 20 sows that were fed a commercially acceptable swine ration as a control ration. The treated group of 9 sows was fed the control ration supplemented with 2 lbs. per ton of the probiotic mixture identified above.

TABLE 3

Analyzed values of the manure (dry matter basis) of sows comparing control diet and diet including mixture of probiotics for three weeks prior to sampling

| Analysis | Farrowing Feed | Farrowing Control Feces | Farrowing Probiotic Feces |
|---|---|---|---|
| % Moisture | 0.0 | 0.00 | 0.00 |
| % Dry Matter | 100.00 | 100.00 | 100.00 |
| % Crude Protein | 21.23 | 20.12 | 19.19 |
| % Starch | 45.71 | 2.28 | 1.75 |
| % Calcium | 1.52 | 6.93 | 5.91 |
| % Phosphorus | 1.12 | 4.71 | 4.19 |
| % Magnesium | 0.22 | 1.12 | 1.05 |
| pH | 6.3 | 7.3 | 6.8 |
| Enteric CFU/g | N/A | 84,200,000 | 6,910,000 |

The data in Table 3 show again the marked decrease in the amount of enteric bacteria shed in the manure of animals following three-weeks of treatment with the mixture of probiotics. Less starch, protein, and minerals are in the feces of the treated animals, demonstrating enhanced feed utilization. Also, the pH of the sows fed the mixture of probiotics is lowered, resulting in an environment which prefers growth of the probiotics while relatively inhibiting the growth of the enteric bacteria (see FIG. 2).

EXPERIMENT 3

As indicated in Tables 1 and 3, there is an initial increase in the amounts of enteric bacteria shed by animals that have been administered the mixture of probiotics of the present invention, followed sometime later by a reduction in the amount of such bacteria being shed by the treated animals relative to control animals. The amount of enteric bacteria shed over time was measured and the results are presented in FIG. 1. The data in FIG. 1 were compiled from swine trials comparing pigs fed a control diet with pigs fed the control diet supplemented with the mixture of probiotics of the present invention. The enteric bacteria shed by the control pigs is represented in the figure by the baseline at 0. The data show that there is an initial, almost immediate increase in enteric bacterial shedding which peaks at about 6 to 8 days, followed by a generally linear decrease to about 28 days and a continuing, though less steep, decrease thereafter. The probiotic mixture is observed to cause an immediate shedding of the existing contamination of enteric bacteria from the gut of the treated animals followed by a very marked decline in the population of the enteric bacteria in the treated animal down to approximately nine times lower than the level of enteric bacterial contamination of the control animals.

EXPERIMENT 4

The lactic acid-producing bacteria included in the mixture of probiotics prefer a lower pH environment than do the enteric bacteria. This is shown in the data presented in FIG. 2. Using a culture substrate of soy protein and glucose as set out in Table 4, the growth rate of various gut pathogens over a range of pH was measured and compared to the growth rate of the mixture of probiotics.

TABLE 4

Culture Media Substrate
(pH adjusted from 7.00 through 4.88 with 12N hydrochloric acid)

| Media (Ingredient) | Per liter (grams) |
| --- | --- |
| Bacto-Soytone (Difco) | 15.0 |
| Dextrose | 6.0 |
| Maltose | 6.0 |
| Sodium Chloride | 5.0 |
| Dipotassium phosphate | 5.0 |
| Monopotassium phosphate | 1.0 |
| Monosodium phosphate | 3.0 |
| De-ionized water | 1,000.0 |

Figure 5:
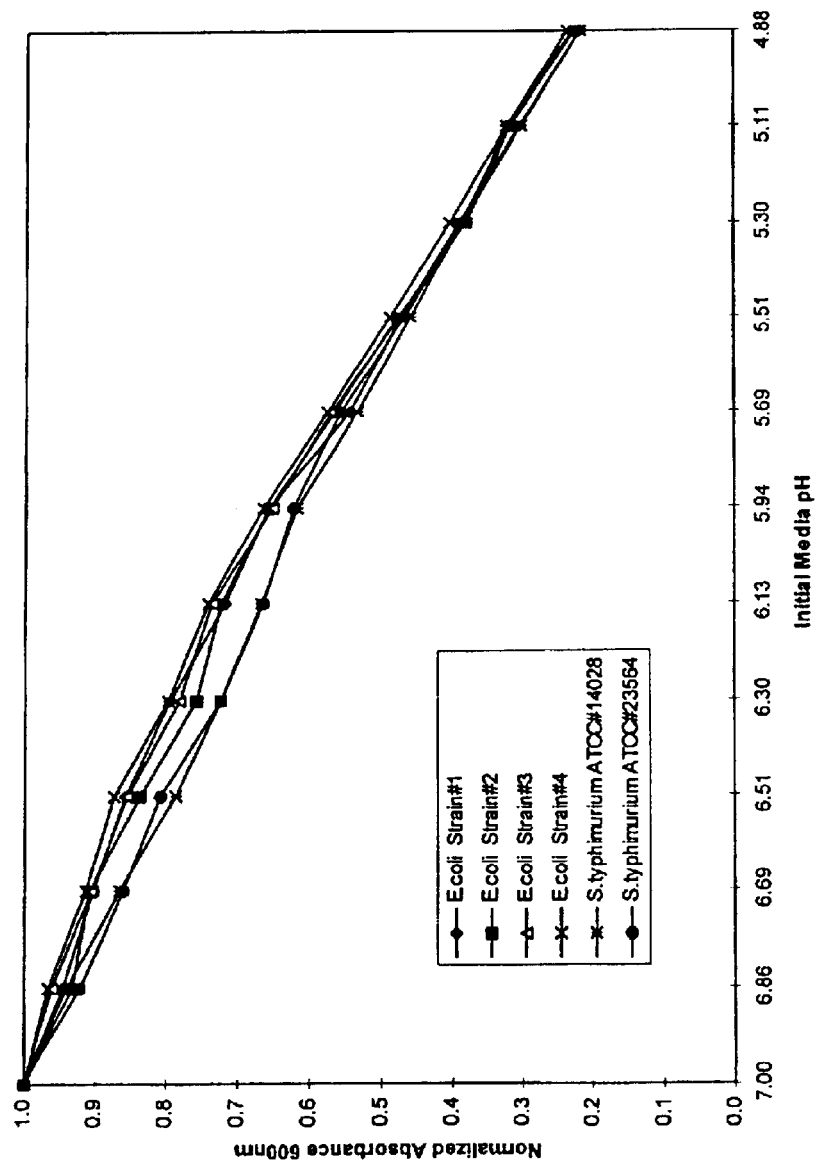
FIG. 5 is a graphical representation of data showing the decline in growth rate with pH of four strains of *E. coli* and two strains of *Salmonella* enteric bacteria.

As can be seen in FIG. 2, the enteric bacteria have a growth rate which declines as the pH falls from neutral (7.2) to a pH of 5, whereas the probiotic growth rate increased until a pH of about 5.8. A similar test was conducted using the same substrate to observe the pH dependence of growth rates of four strains of *E. coli* and two accessions of strains of *Salmonella* (FIG. 5). Each of the *E. coli* and *Salmonella* strains, when normalized to 100% at a pH of 7 showed a generally linear decrease in growth rates down to a pH of 5.

EXPERIMENT 5

A herd of pigs that had a history of chronic infection of *Clostridia* was divided into four groups to observe the effects of treatment with the probiotic mixture before and after farrowing. In the data of Table 5, Group 1 is the control; Group 2 were administered the probiotic mixture between days 7 and 14 following farrowing; and Groups 3 and 4 were administered the probiotic mixture for three weeks before farrowing.

TABLE 5

Data on effects of probiotic mixture on farrowing gilts with chronic Clostridia infections

|  | No. Litters | Total Pigs | No. Pigs Treated for Clostridia | No. of Clostridia deaths | No. of Pigs >8 lbs. | No. of Pigs <8 lbs. | No. of Pigs "No value" | Avg. Pig Wt at 14 days lbs. |
| --- | --- | --- | --- | --- | --- | --- | --- | --- |
| Group 1 | 18 | 160 | 108 | 7 | 146 | 4 | 3 | 10.8 |
| Group 2 | 19 | 158 | 60 | 2 | 154 | 2 | 0 | 12.0 |
| Group 3 | 27 | 216 | 0 | 0 | 216 | 0 | 0 | 11.8 |
| Group 4 | 22 | 120 | 0 | 0 | 118 | 0 | 2 | 12.0 |

TABLE 6

Data on effects of probiotic on pigs born to farrowing gilts with chronic Clostridia infections

|  | Pigs Treated for Clostridia | % Pigs > 8 lbs. |
| --- | --- | --- |
| Group 1 | 67.5 | 91.3 |
| Group 2 | 38.0 | 97.5 |
| Group 3 | 0.0 | 100.0 |
| Group 4 | 0.0 | 98.3 |

Figure 3:
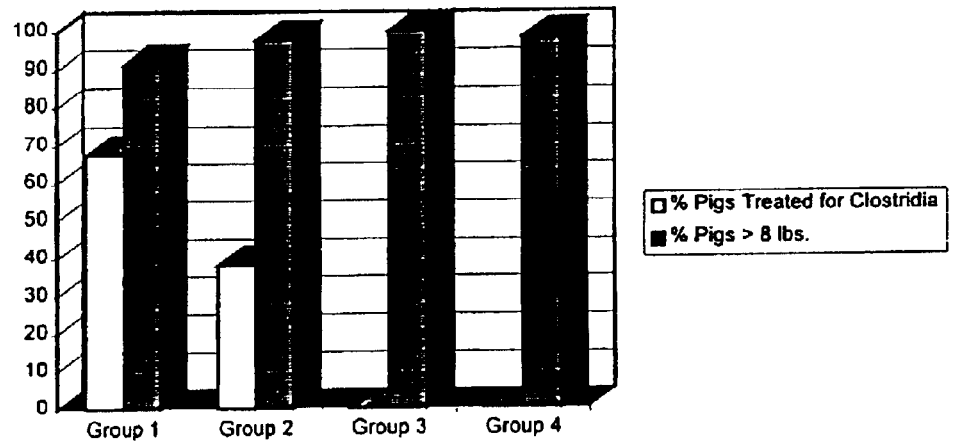
FIGS. 3 and 4 are a graphical representation of data regarding piglets from gilts with chronic *Clostridia* treated with the probiotic mixture of the present invention.
Figure 4:
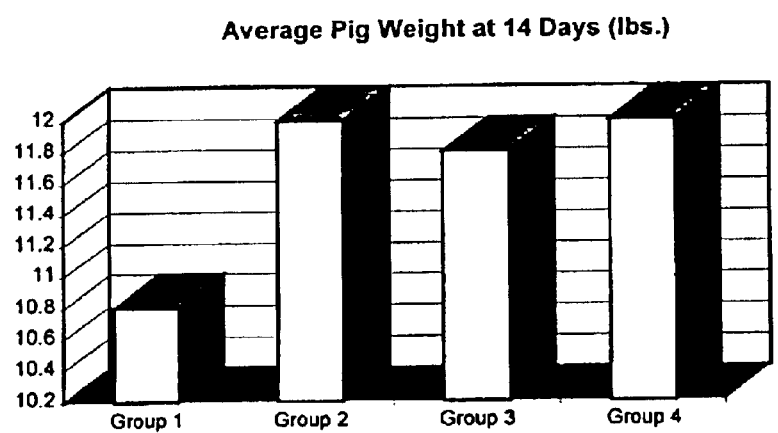

The data show the average litter weights of gilts fed the probiotic mixture was one pound heavier at 14 days compared to the pigs of gilts fed the control diet, and a greater percentage of the piglets born to gilts on the probiotic-treated diet were heavier at 8 lbs. at 14 days. Also, the number of piglets that required treatment for *Clostridia* infections of the treated gilts was lower than piglets of the control gilts. A graphical representation of this summary data is shown in FIGS. 3 and 4.

EXPERIMENT 6

The mixture of probiotics was incubated inside six-inch segments of porcine small intestine to monitor the detachment of enteric bacteria from the intestine tissue over time. A detailed treatment of the trials is shown in Table 7A, and a summary of the results of the trials is presented in Table 7B.

A first trial looked at the effect of the addition of the probiotic upon the indigenous enteric microflora of the small intestine of two different 10 lb. piglets. Two 6-inch ligations of freshly slaughtered small intestine were rinsed three times with 10 mL sterile, phosphate buffered saline (PBS) pH=7.2. The third 10 mL rinse was saved and analyzed for enteric bacteria (using Hektoen-Enteric Agar, BBL). These values are the Time initial (Ti, Pre-addition of Probiotic). A fourth aliquot of PBS (10 mL), $6 \times 10^7$ CFU of the probiotic mixture was added to the 6-inch sections of small intestine. The inoculated intestines were tied-off with sterile surgical string, and incubated at 37° C. for 4 hours in a gently shaking water bath (rpm=65). After 4 hours, the intestinal fluids were collected, rinsed three times with 10 mL PBS and analyzed for enteric bacteria via Hektoen-Enteric Agar (BBL). The results indicated a significant number of enteric bacteria were liberated from the probiotic-treated intestinal sections.

To substantiate the results of the first trial, a second trial with controls was conducted using four 6-inch sections of the illium of the small intestine from a freshly slaughtered 220 lb. hog. Trial 2 looked at the effect of the addition of the probiotic upon the indigenous enteric microflora of the porcine small intestine. A thirty-six inch ligation of porcine small intestine was collected and cut into 6-inch sections. The treatments to the intestine were applied to non-adjacent sections from the original 36-inch ligation (i.e., section 1-control; section 2-probiotic; section 3-control; section 4-probiotic). As in Trial 1, the small intestines were rinsed three times with 10 mL PBS. In the first and third sections, 10 mL of sterile PBS was added; in the second and fourth sections, a 10 mL aliquot of PBS to which had been added $5 \times 10^4$ CFUs of the probiotic mixture was added. The intestine sections were subsequently tied-off and incubated at 37° C. for 4 hours in a gently shaking water bath (65 rpm). After 4 hours, the intestinal fluids were collected, rinsed three times with 10 mL PBS and analyzed for enteric bacteria via HektoenEnteric Agar (BBL). These analyzed values would quantitate the "free" (non-intestinally attached) enteric bacteria. The results of Trial 2 show 2.6 times more enteric bacteria were liberated (on average) from the probiotic-treated sections than the control sections.

TABLE 7A

Total CFUs Added and Collected from Small Intestine Sections

| | Enterics | Yeasts | Enterococci | Total CFU Added |
|---|---|---|---|---|
| Time = 0 Total CFUs Added to 6-inch Section of Small Intestine | | | | |
| Control, Rep #1 | 0 | 0 | 0 | 0 |
| Control, Rep #2 | 0 | 0 | 0 | 0 |
| Probiotic, Rep #1 | 0 | $2.33 \times 10^3$ | $4.8 \times 10^4$ | $5.03 \times 10^4$ |
| Probiotic, Rep #2 | 0 | $2.25 \times 10^3$ | $5.10 \times 10^4$ | $5.33 \times 10^4$ |
| Time = 4 Total CFUs Collected from 6-inch Section of Small Intestine | | | | |
| Control, Rep #1 | $3.40 \times 10^5$ | 0 | $2.83 \times 10^7$ | $2.86 \times 10^7$ |
| Control, Rep #2 | $4.40 \times 10^5$ | 0 | $2.14 \times 10^7$ | $2.18 \times 10^7$ |
| Probiotic, Rep #1 | $8.50 \times 10^5$ | $2.93 \times 10^3$ | $7.41 \times 10^7$ | $7.50 \times 10^7$ |
| Probiotic, Rep #2 | $1.20 \times 10^6$ | $2.14 \times 10^3$ | $8.56 \times 10^7$ | $8.68 \times 10^7$ |

TABLE 7B

Liberated "free" enteric bacteria from porcine intestinal tissue following addition of probiotic mixture

| | Total Enteric CFUs Detached | Relative Amount |
|---|---|---|
| Trial 1 | | |
| Rep 1 | | |
| Pre-addition of probiotic (Ti) | 10,000 | |
| 4 hrs. post-addition | 640,000 | +64 X |
| Rep 2 | | |
| Pre-addition of probiotic (Ti) | 8,000 | |
| 4 hrs. post-addition | 204,000 | +25 X |
| Trial 2 | | |
| Rep 1 | | |
| 4 hrs. (untreated) | 340,000 | |
| 4 hrs. post-addition | 850,000 | +2.5 X |
| Rep 2 | | |
| 4 hrs. (untreated) | 440,000 | |
| 4 hrs. post-addition | 1,200,000 | +2.7 X |

EXPERIMENT 7

An experiment was conducted to quantitate the production of lactic acid by the two strains of *Enterococci* used in the probiotic mixture of the preferred embodiment of the invention. The bacteria were grown on a soy protein/sugar substrate wherein the three sugars lactose, glucose and maltose were used. The substrates were made up as shown in Table 8.

TABLE 8

Culture Media Substrate
(pH = 6.9 +/− 0.1 units)

| Media (Ingredient) | Per liter rams |
|---|---|
| Bacto-Soytone (Difco) | 15.0 |
| Carbohydrate source | 10.0 |
| Sodium Chloride | 3.6 |
| De-ionized water | 1,000.0 |

Figure 6:
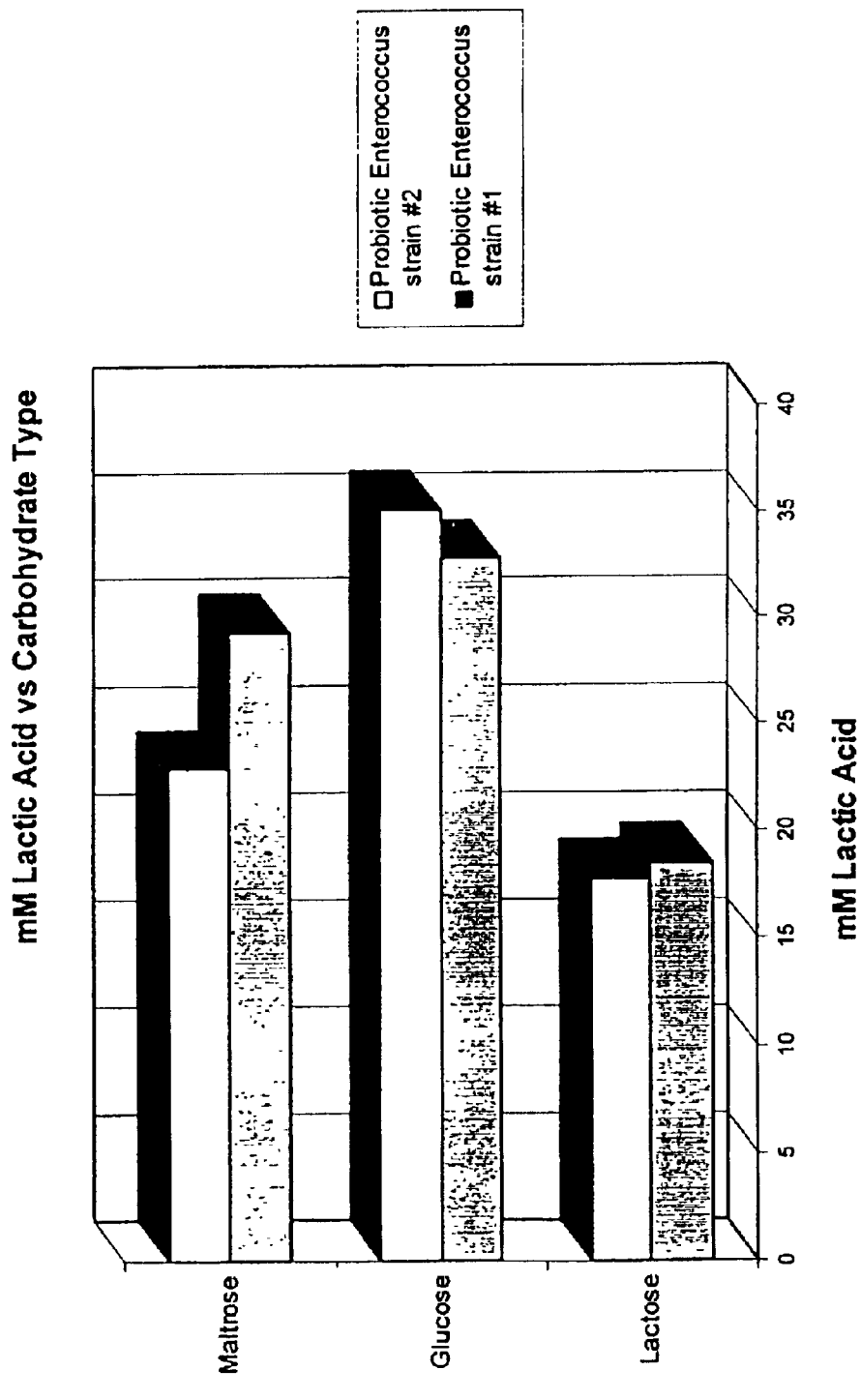
FIG. 6 is a graphical representation of the production of lactic acid by the two different *Enterococci* bacteria strains used in the preferred embodiment of the present invention in the presence of lactose, glucose, and maltose.

Five mL of the media was inoculated with $10^5$ CFUs of the bacteria. The substrates were incubated at 37° C. for 21 hrs and the concentration of lactic acid was measured. The lactic acid was analyzed by capillary electrophoresis (Beckman 5510 series), using 10 mM benzoic acid and 0.5 mM CTAB (hexadecyltrimethylammonium bromide) buffer (pH=4.94), kV=15, open capillary. The results are illustrated in FIG. 6.

EXPERIMENT 8

An experiment was conducted to observe the use of lactose as a carbohydrate source for lactic acid production and growth of the probiotic strains of *Enterococcus* and its utilization or non-utilization by the other microbes tested. The microbes were grown on the media set out in Table 9.

TABLE 9

Culture Media Substrate
(pH = 6.9 +/− 0.1 units)

| Media (Ingredient) | Per liter rams |
|---|---|
| Bacto-Soytone (Difco) | 15.0 |
| Lactose | 10.0 |
| Sodium Chloride | 3.6 |
| De-ionized water | 1,000.0 |

In the experiment, 5 mL of the media was inoculated with $10^4$ CFUs of the respective strain of microbe. The substrates were incubated at 37° C. for 18 hrs and the concentration of lactic acid was measured. The lactic acid was analyzed by capillary electrophoresis (Beckman 5510 series), using 10 mM benzoic acid and 0.5 mM CTAB (hexadecyltrimethylammonium bromide) buffer (pH=4.94), kV=15, open capillary. The results are illustrated in Table 10.

TABLE 10

Lactic Acid Production of Strains of Various Microbes

| ATCC # | Microbial ID | MM lactic acid (18 hrs at 37° C.) |
|---|---|---|
|  | Probiotic Enterococcus strain #1 | 13.3 |
|  | Probiotic Enterococcus strain #2 | 15.6 |
| 25931 | Shigella sonnei | 2.1 |
| 11835 | Shigella dysenteriae | 0[1] |
| 23564 | Salmonella typhimurium | 0[1] |
| 14028 | Salmonella typhimurium | 0[1] |
| 43888 | Escherichia coli 0157:H7 | 4.4 |
| 10145 | Pseudomonas aeruguinosa | 0[1] |
| 29428 | Campylobacter jejuni | 0[1] |
| 9689 | Clostridium difficile | 0[1] |
| 14034 | Vibrio cholerae | 0[1] |

[1]Detection limit is 0.1 mM, values less than 0.1 mM are given as 0.

EXPERIMENT 9

An experiment was conducted to observe the adherence of various bacterial strains to the *Saccharomyces* yeast strains used in the probiotic mixture of the present invention. The bacterial strains tested are listed in Table 11.

TABLE 11

Bacterial Strains

| ATCC # | Microbe Tested |
|---|---|
| 25931 | Shigella sonnei |
| 23564 | Salmonella typhimurium |
| 14028 | Salmonella typhimurium |
| 43888 | Escherichia coli 0157:H7 |
| 10145 | Pseudomonas aeruguinosa |
| 29428 | Campylobacter jejuni |
| 9689 | Clostridium difficile |

The *Saccharomyces* yeast strains of the probiotic mixture and the bacterial strains tested were grown on appropriate media, as listed below and in the following Tables 12 and 13.

TABLE 12

Culture Media Substrate for Saccharomyces Yeast Strains (pH = 6.9 +/− 0.1 units)

| Media (Ingredient) | Per liter (grams) |
|---|---|
| Trypticase soy broth | 8.0 |
| Dextrose | 8.0 |
| Sucrose | 8.0 |
| Malt Extract | 8.0 |
| De-ionized water | 1,000.0 |

TABLE 13

Culture Media Substrate for Salmonella, Escherichia, Shigella and Klebisella species (pH = 7.0 +/− 0.2 units)

| Media (Ingredient) | Per liter rams |
|---|---|
| Pancreatic digest of casein | 10.0 |
| Dextrose | 3.0 |
| Sodium chloride | 5.0 |
| Yeast extract | 5.0 |
| Calcium chloride | 1.0 |
| De-ionized water | 1,000.0 |

For other species, commercial media were used: *Clostridium* species—Reinforced Clostridial Medium (Difco); *Campylobacter* species—Fluid Thioglycollate Medium (Difco); *Pseudomonas* species—Trypticase Soy Broth (BBL).

All cultures were grown for 18 hrs at 37° C. in the appropriate medium. The organisms were centrifuged at 7,000 rpm for 30 minutes and washed twice with PBS (pH=7.2). After the second wash, the cells were resuspended in PBS to produce a McFarland #2 standard of turbidity. Next, 0.2 mL of the appropriate bacterial resuspension and 0.1 mL of the *Saccharomyces* resuspension were co-incubated for 5 mins at 37° C. in a shaking water bath (rpm=65). After shaking, the mixtures were held at 4° C. for 4 hrs. The mixed cultures were Gram-stained and a sample deposited on a microscope slide. The stained slides were observed under 1,500 magnification to determine the interaction between the bacterial strains being tested and the *Saccharomyces*. Adherence of the bacteria to the *Saccharomyces* strains was observed for all bacterial species.

EXPERIMENT 10

An experiment was conducted to observe the lactic acid and acetic acid production over time of a strain of *E. coli*, the *Enterococci* species of the probiotic mixture, the *Saccharomyces* species of the probiotic mixture alone and in combination with the *E. coli* strain. In the experiment, $10^7$ CFUs of each microbe were added to 250 mL of the media culture set out in Table 14.

TABLE 14

Culture Media Substrate (pH = 7.0 +/− 0.1 units)

| Media (Ingredient) | Per liter rams |
|---|---|
| Bacto-So one Difco) | 5.0 |
| Dextrose | 1.0 |
| Maltose | 3.5 |
| Sodium Chloride | 3.6 |
| Di otassium phosphate | 1.0 |
| T ticase so broth BBL | 1.0 |
| Soluble starch | 0.5 |
| De-ionized water | 1,000.0 |

Ten mL aliquots were taken and analyzed prior to inoculation (at 37° C. in a gently shaking water bath at 65 rpm) and at 2, 4, 6 and 8 hrs post-inoculation. The lactic acid was analyzed by capillary electrophoresis (Beckman 5510 series), using 10 mM benzoic acid and 0.5 mM CTAB (hexadecyltrimethylammonium bromide) buffer (pH=4.94), kV=15, open capillary. The results are set out in Table 15.

TABLE 15

Lactic Acid and Acetic Acid Production Over Time

| Culture ID | 0 hr | 2 hrs | 4 hrs | 6 hrs | 8 hrs |
|---|---|---|---|---|---|
| | | mM lactic acid | | | |
| E. coli ATCC #43888 (only) | 0.0[1] | 0.3 | 0.8 | 1.4 | 2.6 |
| Probiotic Enterococci mixture (only) | 0.0[1] | 0.8 | 4.2 | 8.1 | 13.9 |
| Probiotic Saccharomyces mixture (only) | 0.0[1] | 0.0[1] | 0.0[1] | 0.0[1] | 0.0[1] |
| E. coli + Enterococci | 0.0[1] | 0.7 | 4.3 | 8.4 | 14.2 |
| E. coli + Saccharomyces | 0.0[1] | 0.3 | 0.8 | 1.4 | 2.5 |
| | | mM acetic acid | | | |
| E. coli ATCC #43888 (only) | 0.0[1] | 0.6 | 1.0 | 2.4 | 3.5 |
| Probiotic Enterococci mixture (only) | 0.0[1] | 0.0[1] | 0.0[1] | 0.0[1] | 0.0[1] |
| Probiotic Saccharomyces mixture (only) | 0.0[1] | 0.0[1] | 0.0[1] | 0.0[1] | 0.0[1] |
| E. coli + Enterococci | 0.0[1] | 0.6 | 1.1 | 1.8 | 2.7 |
| E. coli + Saccharomyces | 0.0[1] | 0.7 | 1.1 | 2.4 | 3.6 |

[1]Detection limit is 0.1 mM, values less than 0.1 mM are given as 0.

These results suggest that the ability of the *Enterococci* strains of the probiotic mixture to produce lactic acid are not hindered nor greatly influenced by the *E. coli* isolate. Also, ability of the *E. coli* isolate to metabolize appears to be hindered when co-incubated with the *Enterococci* as seen in the acetic acid results at 6 and 8 hrs and the marked depression of acetic acid formation relative to *E. coli* only and to *E. coli+Saccharomyces*. At 6 hrs and beyond, the lactic acid concentration was greater than 8 mM. Further, the *Saccharomycecs* strains do not seem to hinder the ability of the *E. coli* isolate to metabolize and produce acids.

EXPERIMENT 11

This experiment shows the unexpected, synergistic probiotic effect of using both *Enterococcus* and *Saccharomyces* strains in a single probiotic product.

Non-Swiss Albino female mice (CF-1) from Harlan Sprague-Dawley (Indianapolis, Ind.) were challenged with *Salmonella typhimurium* ATCC#14028. The mice were three-week old and barrier-raised. *Salmonella typhimurium* did not cause 100% fatality in CF-1 strain mice, but did create mouse morbidity. An ad libitum commercial diet (Harlan Teklad, Madison, Wis.), containing 16% crude protein, 3.5% fat, 6.5% crude fiber and autoclaved deionized water, were used to feed the mice.

Each mouse treatment group was housed in a separate "Micro-Barrier" isolation unit (Allentown Caging Equipment, Allentown, N.J.). Each unit contained a removable wire floor. The floor acted as the walkway and allowed the urine to pass. Feces was collected daily from each individual mouse.

Xylose Lysine Desoxycholate (XLD) agar (Difco) was used to determine *Salmonella* CFUs. On XLD agar, the *Salmonella typhimurium* challenge strain grew as colonies which appeared red with black centers while other enteric Gram-negative bacilli appeared as yellow colonies without black centers. Incubation conditions were at 36° C. for 24 hours, aerobically. *Salmonella* confirmation was determined via immobilization in motility medium by polyvalent H (flagellar) antibodies (*Salmonella* 1-2 Test, BioControl, Bellevue, Wash.).

Potato Dextrose Agar (BBL) supplemented with tartaric acid (1.4 g/liter) was used to determine fecal *Saccharomyces* (yeast) populations. Incubation conditions were at 30° C. for 72 hours, aerobically. *Enterococcosel* Agar (Becton-Dickinson) was used to determine fecal *Enterococcus* concentrations. Incubation conditions were at 36° C. for 24 hours, aerobically.

Probiotic microbes were grown in Brain Heart Infusion (BHI) Broth (Becton-Dickinson) overnight. After overnight growth, the probiotic cells were centrifuged at 2,000×g for 15 minutes and washed twice with pre-sterilized phosphate-buffered saline (PBS, pH=7.2) and resuspended in BHI to a standardized concentration (via pre-determined optical density vs CFU/mL data) of $2\times10^8$ CFU per 100 µL. Probiotic organisms were then orally dosed with 100 µL probiotic microbes via gastric tube to supply $2\times10^8$ CFU per mouse. The appropriate treatment was given prior to the *Salmonella* challenge (beginning 1 day prior to *Salmonella* challenge) and daily thereafter through 7 days post-challenge. Control mice were dosed with 100 µL BHI only.

The combination treatments using both *Enterococcus* and *Saccharomyces* strains were also orally dosed via gastric probe using washed microbial cells resuspended in BHI according to the above protocol. A total of $2\times10^8$ per mouse per day ($1\times10^8$ CFU *Enterococcus* species plus $1\times10^8$ CFU *Saccharomyces* species, CFU=colony forming units) in 100 µL of diluent (diluent=BHI) was administered. The appropriate treatment was given prior to the *Salmonella* challenge (beginning 1 day prior to *Salmonella* challenge) and daily thereafter through 7 days post-challenge.

Probiotic strains used in various treatment groups included *Enterococcus faecium* NCIMB #10415 (for Treatment 1, supplied by Cerbios-Pharma, S A, Barbengo, Switzerland. NCIMB=National Collection of Industrial, Food and Marine Bacteria, 23 St. Machar Drive, Aberdeen AB2 1RY, Scotland, United Kingdom), *Enterococcus casseiflavus* ATCC #51328 (for Treatment 2, supplied by the American Type Culture Collection (ATCC), Manassas, Va., USA), *Enterococcus avium* ATCC #14025 (for Treatment 3), *Saccharomyces cerevisiae* ATCC #32167 (for Treatment 4), *Saccharomyces bayanus* ATCC #36022 (for Treatment 5), *Saccharomyces boulardii* CNCM# I-1079(for Treatment 6, supplied by Lallemand, Inc., Ontario, Canada. CNCM= Collection Nationale De Cultures De Microorganisms, Institut Pasteur, 28 rue du Dr Roux, 75724 Paris Cedex 15, France), *Enterococcus faecium* NCIMB #10415 plus *Saccharomyces bayanus* ATCC #36022 (for Treatment 7), *Enterococcus casseiflavus* ATCC #51328 plus *Saccharomyces boulardii* CNCM# I-1079 (for Treatment 8), *Enterococcus avium* ATCC #14025 plus *Saccharomyces cerevisiae* ATCC #32167 (for Treatment 9), and untreated control (100 µL of diluent (BHI) only) (for Treatment 10).

*Salmonella typhimurium* ATCC# 14028 (ST) cells were grown overnight at 37° C. in BHI broth. After overnight growth, the *Salmonella* cells were centrifuged at 2,000×g for 15 minutes and washed twice with pre-sterilized phosphate-buffered saline (PBS, pH=7.2). The *Salmonella* cells after the final PBS wash were resuspended in BHI, 100 µL of which was orally inoculated via gastric probe to each mouse. The 100 µL *Salmonella* dose delivered $5\times10^8$ viable CFU per mouse.

Data was analyzed using the Analysis of Variance procedure of SAS, Release 6.12, SAS Institute, Cary, N.C. Means were tested by least significant difference (LSD) to identify differences among groups.

Ten (10) treatment groups consisting of 5 mice per treatment group were challenged with ST orally. The treatment groups varied by the probiotic microorganism or combination of microorganisms administered.

Antibiotics were added to the drinking water prior to the administration of the probiotic microbes (*Enterococcus* and *Saccharomyces*) to reduce the indigenous enteric microflora and thus exam the "protective" effects of the probiotic organisms versus the *Salmonella* challenge. Antibiotics used in the drinking water was a cocktail (Ab) of Streptomycin, Vancomycin, Oxytetracycline, Amphotericin B (2.5 mg, 125 $\mu$g, 100 $\mu$g and 0.5 mg per mL respectively) beginning 5 days pre-ST challenge (−5d) and ending 2 days pre-ST challenge (−2d).

Feces was individually collected from each mouse between hours 8–10 a.m. daily and analyzed beginning 1 day pre-ST challenge (−1d) and ending 7 days post-ST challenge (+7d). The day of the one-time *Salmonella* challenge was designated as "0S.t.".

Fecal samples were aseptically collected and serially diluted using PBS. Microbial analysis was subsequently performed. The effect of the *Salmonella* challenge on mortality, growth and murine feces' microbiology was examined. To determine murine growth, individual weights were recorded on the day of the challenge pre-ST (on 0S.t.), and 7 days post-ST challenge ($T_{+7d}$). Mortality was record daily.

Figure 7:
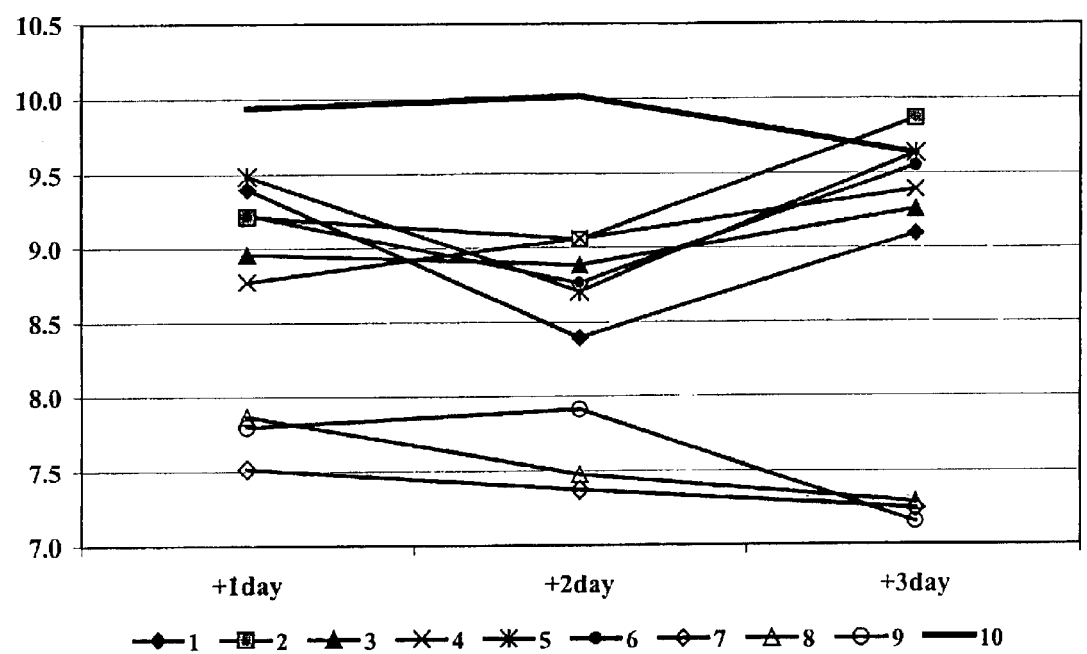
FIG. 7 depicts the mean of the viable *Salmonella* CFU (expressed in logarithms) per gram of dry matter corrected feces (DM corrected) during the first three days following the ST challenge.
Figure 8:
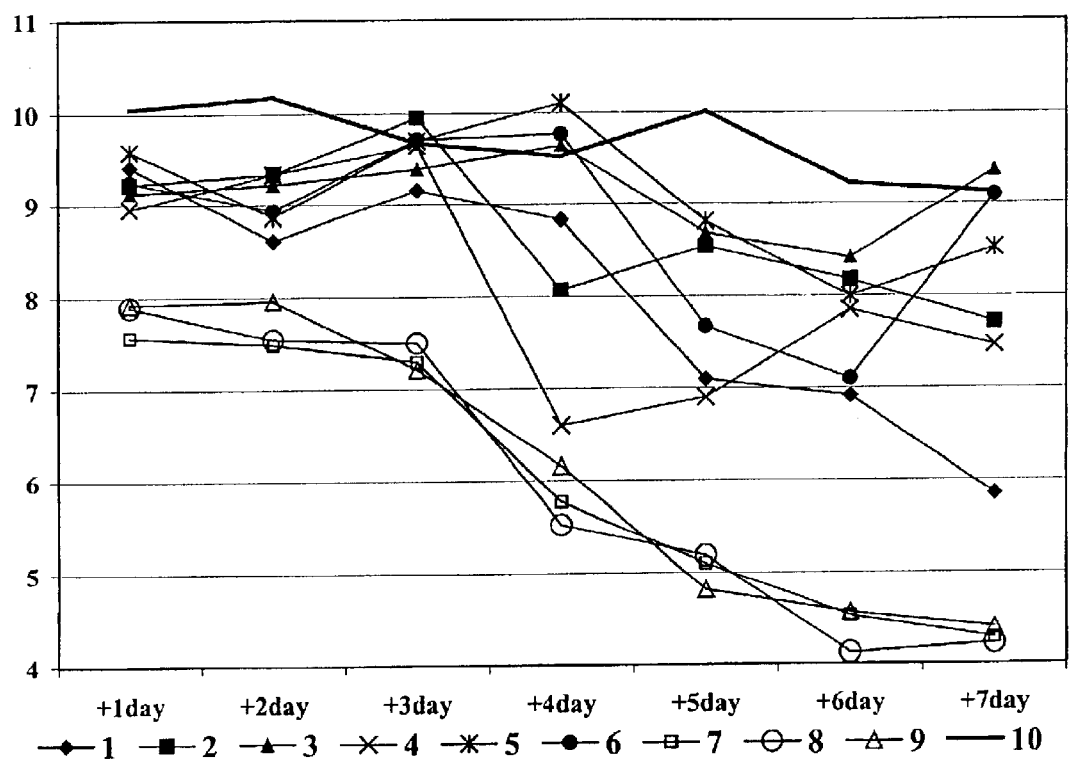
FIG. 8 shows the mean of the viable *Salmonella* CFU (expressed in logarithms) per gram of dry matter corrected feces during the first seven days following the ST challenge.
Figure 9:
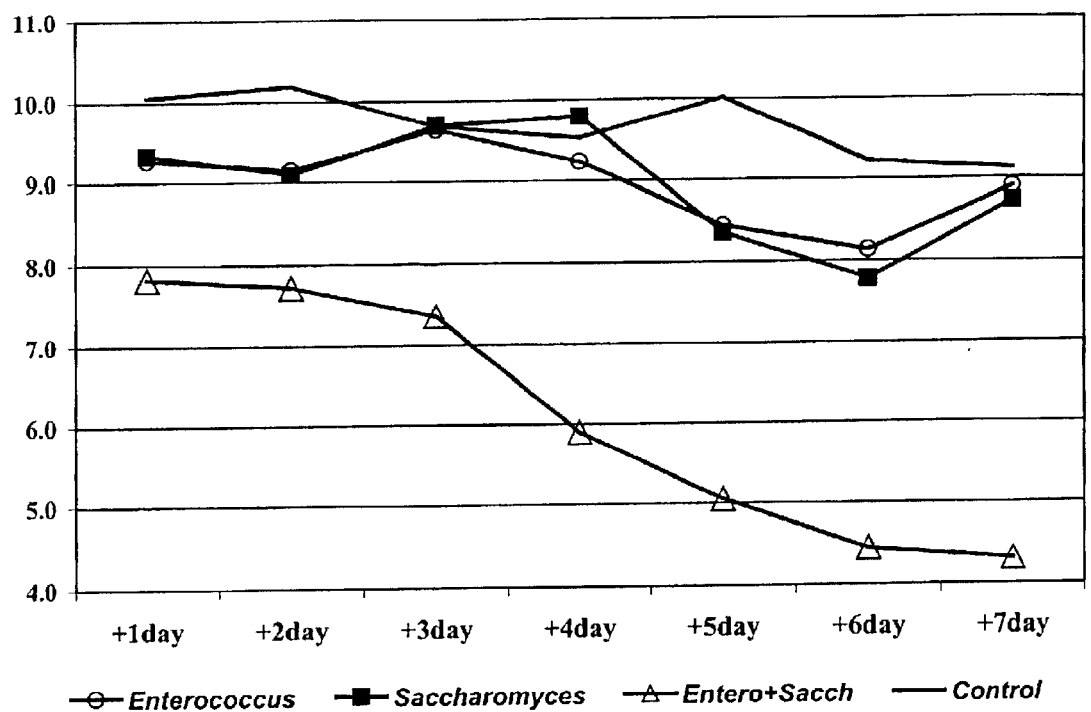
FIG. 9 is the compiled mean of the viable *Salmonella* CFU (expressed in logarithms) per gram of dry matter corrected feces during the first seven days following the ST challenge.

Mice for this trial were randomized from the same mouse pool. FIGS. 7, 8 and 9 as well as Tables 16, 17, 18 and 19 compare and contrast the treatment of the mice with the individual microbes, *Enterococcus* or *Saccharomyces*, versus the combination of *Enterooccus* and *Saccharomyces*.

TABLE 16

Study Timeline

| Time ($T_x$) | Action |
| --- | --- |
| $T_{-5d} - T_{-2d}$ | Abs used in drinking water through evening of $T_{-2d}$ when Abs removed. |
| $T_{-1d}$ | Fecal microbiology performed. Probiotic treatments administered. |
| $T_{0\ s.t.}$ | Mice weighed. Fecal microbiology performed. Probiotic treatments administered. ST administered. |
| $T_{+1d} - T_{+7d}$ | Fecal microbiology performed. Probiotic treatments administered. |
| $T_{+7d}$ | Mice weighed. |

TABLE 17

Microbial Profile of Mouse Feces Collected After One Probiotic Treatment (collected from day = 0 S.t. (prior to ST challenge), logarithm CFU/g feces (DM corrected))

| Treatment | Enterobacteriaceae | Salmonella spp. | Enterococci | Yeasts |
| --- | --- | --- | --- | --- |
| 1 | <2 | None detected | 10.10 | <2 |
| 2 | <2 | None detected | 9.76 | <2 |
| 3 | <2 | None detected | 10.00 | <2 |
| 4 | <2 | None detected | 2.41 | 6.70 |
| 5 | <2 | None detected | 2.39 | 7.28 |

TABLE 17-continued

Microbial Profile of Mouse Feces Collected After One Probiotic Treatment (collected from day = 0 S.t. (prior to ST challenge), logarithm CFU/g feces (DM corrected))

| Treatment | Enterobacteriaceae | Salmonella spp. | Enterococci | Yeasts |
| --- | --- | --- | --- | --- |
| 6 | <2 | None detected | 2.19 | 7.52 |
| 7 | <2 | None detected | 10.39 | 6.88 |
| 8 | <2 | None detected | 10.40 | 7.36 |
| 9 | <2 | None detected | 10.41 | 7.04 |
| 10 | <2 | None detected | 2.21 | <2 |

TABLE 18

Statistical Analysis of Individual and Combination of Ingredients Results (logarithm of statistical means of viable fecal Salmonella concentration (DM corrected) from periods: +1 day only, +3 days only, compilation of +1 through +3 days and compilation of +1 through +7 days post-Salmonella challenge[1])

| Treatment | +1 day | +3 day | +1 thru +3 days | +1 thru +7 days |
| --- | --- | --- | --- | --- |
| 1 | 9.396$^b$ | 9.092$^c$ | 8.961$^c$ | 7.978$^b$ |
| 2 | 9.214$^{bc}$ | 9.862$^a$ | 9.378$^b$ | 8.715$^{ab}$ |
| 3 | 8.956$^{cd}$ | 9.255$^{bc}$ | 9.031$^c$ | 9.117$^{ab}$ |
| 4 | 8.773$^d$ | 9.388$^{abc}$ | 9.075$^{bc}$ | 8.103$^b$ |
| 5 | 9.485$^b$ | 9.634$^{ab}$ | 9.275$^{bc}$ | 9.080$^{ab}$ |
| 6 | 9.227$^{bc}$ | 9.550$^{abc}$ | 9.180$^{bc}$ | 8.789$^{ab}$ |
| 7 | 7.516$^e$ | 7.248$^d$ | 7.378$^d$ | 6.001$^c$ |
| 8 | 7.865$^e$ | 7.285$^d$ | 7.542$^d$ | 5.996$^c$ |
| 9 | 7.795$^e$ | 7.154$^d$ | 7.620$^d$ | 6.144$^c$ |
| 10 | 9.939$^a$ | 9.634$^{ab}$ | 9.862$^a$ | 9.684$^a$ |

[1]Values are resultant means from specified periods. Values in the same column with different superscripts are significantly different (p < 0.05).

TABLE 19

Mouse Weight and Mortality

| Treatment | Mouse Wt[1], 0 S.t., g | Mouse Wt[1], +7 d, g | Livability +14 d, n/5[2] |
| --- | --- | --- | --- |
| 1 | 21.39$^a$ | 19.23$^b$ | 5/5 |
| 2 | 20.05$^a$ | 15.09$^d$ | 3/5 |
| 3 | 21.12$^a$ | 16.50$^{cd}$ | 3/5 |
| 4 | 20.43$^a$ | 18.37$^{bc}$ | 5/5 |
| 5 | 21.08$^a$ | 18.59$^{bc}$ | 4/5 |
| 6 | 21.61$^a$ | 18.99$^{bc}$ | 4/5 |
| 7 | 20.17$^a$ | 20.67$^{ab}$ | 5/5 |
| 8 | 21.22$^a$ | 22.18$^a$ | 5/5 |
| 9 | 21.49$^a$ | 21.81$^a$ | 5/5 |
| 10 | 21.49$^a$ | 19.01$^{bc}$ | 4/5 |

[1]Values are resultant means of individual mouse weights from specified period. Values in the same column with different superscripts are significantly different (p < 0.05).
[2]Mortality is expressed as n of 5 (Five (5) mice per treatment group began the study pre-ST). Probiotic treatments were ceased after $T_{+7\ days}$.

FIG. 7 is the mean of the viable *Salmonella* CFU (expressed in logarithms) per gram of dry matter corrected feces (DM corrected) during the first three days following the ST challenge. The result of each treatment is represented by a data line. FIG. 8 is the mean of the viable *Salmonella* CFU (expressed in logarithms) per gram of dry matter corrected feces during the first seven days following the ST challenge. The result of each treatment is represented by a data line. FIG. 9 is the compiled mean of the viable *Salmonella* CFU (expressed in logarithms) per gram of dry matter corrected feces during the first seven days following the ST challenge. The result for each treatment type is represented by a data line.

Fecal microbiological analysis from individual mice taken on $T_{-1d}$ demonstrated the effect of the antibiotics within the drinking water (data not shown). All mice possessed less than the detectable limit (<100 CFU) of *fecal enterococci*, yeasts, and Gram-negative rods. Also, using enrichment techniques, *Salmonella* species were not detected.

Table 17 displays that the probiotic organisms impact the fecal microbiology of the mouse after only one oral dose. That is, the respective treatment microbe-type was observed in fairly high quantities in the fecal material.

Table 18 and FIGS. 7 and 8 display the symbiotic effect of the combination of the *Enterococcus* and *Saccharomyces* species on the reduction of viable *Salmonella* in the mouse feces. Mouse weight statistics and mortality data from Table 19 demonstrate that *Salmonella* challenge has less effect on the growth and mortality of the mice treated with the combination of *Enterococcus* and *Saccharomyces*, as compared to either the control, *Enterococcus* only treatments or *Saccharomyces* only treatments. That is, the *Salmonella* infection would lead to mouse mortality or morbidity. Morbidity led to a decrease in average mouse weight.

Mice treated daily with the combinations of *Enterococci* plus *Saccharomyces* (Treatments 7, 8 and 9) had statistically lower viable *Salmonella* in their fecal material compared to the control (Treatment 10), *Enterococcus* only (Treatments 1, 2 and 3) and *Saccharomyces* only (Treatments 4, 5 and 6) dosed mice. A more rapid *Salmonella* clearing effect was observed in the *Enterococci* plus *Saccharomyces* treated mice (Treatments 7, 8 and 9).

Statistically, there is a synergy in combining *Enterococcus* and *Saccharomyces* as compared to either *Enterococcus* alone or *Saccharomyces* alone (see, e.g., FIG. 9). The synergy is not based on merely the total probiotic CFUs dosed to each mouse, but rather the combination of *Enterococcus* and *Saccharomyces*. This phenomenon is apparent from the fact that all mice, except the control mice, were gavaged daily with the same total CFU dosage ($2 \times 10^8$).

Mice dosed with the combination of *Enterococcus* plus *Saccharomyces* CFUs statistically weighed more than those treated with *Enterococcus* only, *Saccharomyces* only or the controls at $T_{+7\ days}$ (i.e. mice given Treatments 7, 8 and 9 were less morbid than other study mice). Treatments 7, 8 and 9 gained weight during the 7 days following the ST challenge. No statistical difference in mouse weight was seen on day=0S.t.

Although the invention has been described with respect to a preferred embodiment thereof, it is to be also understood that it is not to be so limited since changes and modifications can be made therein which are within the full intended scope of this invention as defined by the appended claims.

What is claimed is:

1. A probiotic product comprising:
   (a) one or more *Enterococcus* strains;
   (b) one or more *Saccharomyces* strains; and
   (c) one or more carbohydrate sources capable of being used by said one or more *Enterococcus* strains as a food source for growth,
   wherein the probiotic product is suitable for oral administration to humans or monogastric animals to control enteric bacteria populations in the intestines of said humans or monogastric animals, and wherein between 5% and 50% of the total colony forming units (CFUs) of the probiotic product are CFUs produced by said one or more *Saccharomyces* strains, and between 50% and 95% of the total CFUs of the probiotic product are CFUs produced by said one or more *Enterococcus* strains.

2. A method for preventing or reducing the contamination of enteric bacteria in a human or monogastric animal, comprising the steps of:
   (a) preparing a probiotic product comprising:
      one or more *Enterococcus* strains;
      one or more *Saccharomyces* strains; and
      one or more carbohydrate sources capable of being used by said one or more *Enterococcus* strains as a food source for growth,
      wherein the probiotic product is suitable for oral administration to humans or monogastric animals to control enteric bacteria populations in the intestines of said humans or monogastric animals, and wherein between 5% and 50% of the total colony forming units (CFUs) of the probiotic product are CFUs produced by said one or more *Saccharomyces* strains, and between 50% and 95% of the total CFUs of the probiotic product are CFUs produced by said one or more *Enterococcus* strains; and
   (b) orally administering said probiotic product to the human or monogastric animal in an amount and on a schedule effective to reduce the contamination of enteric bacteria.

3. The method according to claim 2, wherein the carbohydrate is one or more sugars selected from the group including glucose, fructose, lactose, maltose, and sucrose.

4. The method according to claim 2, wherein *Enterococcus* is *Enterococcus faecium* 11181 (NCIMB #11181) and one or more *Saccharomyces* strains is one or more strains of the species *Saccharomyces cerevisiae* selected from the group including strains Sc 47 (NCYC #47) and I-1079 (CNCM #I-1079).

* * * * *

UNITED STATES PATENT AND TRADEMARK OFFICE
CERTIFICATE OF CORRECTION

PATENT NO. : 6,841,149 B1
DATED : January 11, 2005
INVENTOR(S) : Spangler et al.

It is certified that error appears in the above-identified patent and that said Letters Patent is hereby corrected as shown below:

Title page,
Item [45], Date of Patent, before "Jan. 11, 2005," please add:
-- * --.
Item [*] Notice, please add:
-- This patent is subject to a terminal disclaimer. --

Signed and Sealed this

Tenth Day of May, 2005

JON W. DUDAS
*Director of the United States Patent and Trademark Office*